United States Patent [19]

Ohta et al.

[11] 4,148,638

[45] Apr. 10, 1979

[54] PHOTOCONDUCTIVE SENSITIVE MATERIAL WITH A TRINITRO-11-INDENO[1,2-b]QUINOXALINE-11-ONE

[75] Inventors: Masafumi Ohta; Mitsuru Hashimoto; Akio Kozima, all of Tokyo, Japan

[73] Assignee: Ricoh Co., Ltd., Tokyo, Japan

[21] Appl. No.: 775,049

[22] Filed: Mar. 7, 1977

[30] Foreign Application Priority Data

Mar. 11, 1976 [JP] Japan .................. 51-26396

[51] Int. Cl.$^2$ .................. G03G 5/06; G03G 5/04; G03G 5/09
[52] U.S. Cl. .................. 96/1.5 R; 96/1.6
[58] Field of Search .................. 260/250 Q; 96/1.5, 1.6

[56] References Cited

U.S. PATENT DOCUMENTS

| | | | |
|---|---|---|---|
| 3,830,647 | 8/1974 | Janssens et al. | 96/1.5 |
| 3,877,935 | 4/1975 | Regensburger et al. | 96/1.5 |
| 3,884,691 | 4/1973 | Rochlitz | 96/1.5 |

FOREIGN PATENT DOCUMENTS 52-52638 4/1977 Japan .................. 96/1.5

*Primary Examiner*—Roland E. Martin, Jr.
*Assistant Examiner*—John L. Goodrow
*Attorney, Agent, or Firm*—Blanchard, Flynn, Thiel, Boutell & Tanis

[57] ABSTRACT

A photoconductive sensitive material composed of a conductive support and a layer consisting essentially of charge-generating pigment, trinitro-11H-indeno[1,2-b]quinoxaline-11-one and binder resin formed on said support, and a photoconductive sensitive material composed of a conductive support, a thin layer consisting of charge-generating pigment alone or mixed with binder resin and a layer consisting essentially of trinitro-11H-indeno[1,2-b]quinoxaline-11-one and binder resin, said two layers being formed in that order on said support, possess high sensitivity and always give a clear-cut image even when used repeatedly.

22 Claims, 2 Drawing Figures

PHOTOCONDUCTIVE SENSITIVE MATERIAL WITH A TRINITRO-11-INDENO[1,2-B]QUINOXALINE-11-ONE

BACKGROUND OF THE INVENTION

The present invention relates to an improvement of photoconductive sensitive materials for use in electrophotography.

Known organic photoconductive substances such as, for instance, poly-N-vinyl carbazole, have recently been considered as materials for use in forming the photoconductive layer of electrophotographic copying materials or image forming element because of their superior film formability and transparency as well as the flexibility of the film formed thereof, but practical use thereof has so far been greatly hampered because they are markedly inferior to inorganic photoconductive substances such as, for instance, zinc oxide, in respect of photosensitivity. Therefore, in order to improve the photosensitivity of such organic photoconductive substances, varieties of sensitizers have been used jointly therewith. Nevertheless, as a matter of fact, no satisfactory organic photoconductive sensitive material has ever been developed.

SUMMARY OF THE INVENTION

A principal object of the present invention is to eliminate the foregoing defects of the prior art and to provide an organic photoconductive sensitive material which possesses a high sensitivity equal to that of the inorganic photoconductive sensitive materials and which is satisfactory for practical use.

Another object of the present invention is to provide an organic photoconductive sensitive material which always gives a clear-cut copied image even when used repeatedly.

A further object of the present invention is to provide a photoconductive sensitive material which facilitates the charging when a film of inorganic photoconductor is applied and has an excellent flexibility.

The present inventors have conducted a series of studies and examinations extending over a long period of time with respect to photoconductive sensitive materials, and they have found that trinitro-11H-indeno[1,2-b]quinoxaline11-one satisfactory properties for use as a charge-transport medium, and the use thereof in combination with appropriate charge-generating pigments provides a photoconductive sensitive material having very desirable properties. The present invention has been accomplished on the basis of this finding.

The photosensitive materials according to the present invention are classified into the following two types.

(1) An organic photoconductive sensitive material prepared by forming a layer consisting essentially of chargegenerating pigment, trinitro-11H-indeno[1,2-b]quinoxaline11-one and binder resin on a conductive support.

(2) An organic photoconductive sensitive material prepared by forming, in the following order, a thin layer consisting of chargegenerating pigment alone or mixed with binder resin and a layer consisting essentially of trinitro-11H-indeno[1,2-b]-quinoxaline-11-one and binder resin on a conductive support.

Said trinitro-11H-indeno[1,2-b]quinoxaline-11-one employed as the charge-transport medium is a compound having the formula

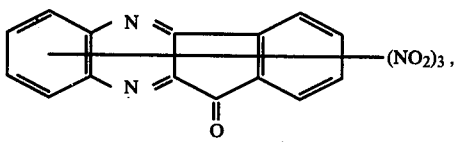

and this compound can be easily synthesized by nitration of 11H-indeno[1,2-b]quinoxaline-11-one or mononitro- or dinitroderivatives thereof by heating at a temperature of 70°- 100°C. usually in the presence of mixed acid. As for the method of synthesis of this compound, particulars thereof have been disclosed in Japanese Patent Application No. 128366/1975, and in the following will be given an example of synthesis of this compound. In this connection, the starting material can be easily obtained by the method taught in, for instance, J. Org. Chem. 27, p.1674 (1962).

EXAMPLE OF SYNTHESIS 24.0 g of 11H-indeno[1,2-b]quinoxaline-11-one (the method of synthesis of this substance was in accordance with the aforesaid literature reference) were dissolved in 400 ml of mixed acid (wherein the fuming nitric acid applied had a specific gravity of 1.50) while cooling with ice. Then, the temperature of the resulting solution was raised gradually, and held at 70°- 80°C. for 3 hours thereby effecting reaction. After letting it cool down, the reaction mixture was put in a large quantity of ice water, and the resulting precipitate was filtered and dried after washing in water. Subsequently, the dried precipitate was dissolved in 600 ml of mixed acid (wherein the fuming nitric acid applied had a specific gravity of 1.52) again, and the temperature of the resulting solution as raised gradually and held at 85°- 90°C. for 5 hours. Then, after adding 180 ml of mixed acid (wherein the fuming nitric acid applied had a specific gravity of 1.52) over about 2.5 hours' period to the solution held at the same temperature as above, the solution was made to react by holding its temperature at about 90°- 92°C. for 5 hours. After letting it cool down, the reaction mixture was put in a large quantity of ice water, and the resulting precipitate was filtered and dried after washing in water. Subsequently, the dried pecipitate was subjected to recrystallization several times by the use of benzene- acetone mixed solvent, whereby 2.8 g of yellow plate crystals were obtained. The melting point of the thus obtained trinitro-11H-indeno[1,2-b]quinoxaline-11-one was in the range of 252.5 - 254.0° C.

As the charge-generating pigment for use in the present invention, organic pigments such as azo dye, xanthene dye, violanthrone dye, phthalocyanine dye, indigoid dye, perylene dye, indanthrone dye, etc. and inorganic pigments such as Se, SeTe, CdS, CdSe, etc. are applicable.

As the binder resin for use in the present invention, varieties of known resins are applicable, and particularly the use of polyester resin, polycarbonate resin, acrylic resin, silicone resin, novolac resin, ketone resin, etc. is desirable. The binder resin does not form a charge-transport complex together with trinitro-11H-indeno-[1,2-b] quinoxaline-11-one.

In the photosensitive material according to the present invention, in addition to the afore-mentioned substances, well-known inorganic or organic photoconductive substances and well-known sensitizers can be used jointly. In this connection, a photoconductive material prepared by combining poly-N-vinyl carbazole or its derivative with trinitro-11H-indeno[1,2-b]quinoxaline-11-one has already been disclosed in the aforesaid Japanese Patent Application No. 128366/1975, and what characterizes the present invention is the additional application of charge-generating pigment to this previously disclosed photoconductive material. In fact, a photoconductive sensitive material prepared by combining a charge-generating pigment having grain size unit expressed by micron with trinitro-11H-indeno[1,2-b]quinoxaline-11-one is unprecedented.

BRIEF DESCRIPTION OF THE DRAWINGS

To explain the present invention by reference to the appended drawings, FIG. 1 and FIG. 2 are respectively enlarged cross-sectional views of examples of the photoconductive sensitive material according to the present invention, in which the reference numeral 1 denotes a conductive support, 2, 2'denote a photosensitive layer, respectively, and 3 denotes a charge-transport layer. The photosensitive material in FIG. 1 is composed of a conductive support 1 consisting of paper or film (e.g., a synthetic resin film deposited with aluminum through evaporation) processed for conductivity or metal plate (e.g., an aluminum plate) and a layer (or photosensitive layer) 2 consisting essentially of charge-generating pigment, trinitro11H-indeno[1,2-b]quinoxaline-11-one and binder resin formed on said support 1. In the case of this photosensitive material, the charge-generating pigment is dispersed in the binder resin in the form of particles having a mean grain size of less than 5μ, preferably less than 1μ. For the photosensitive material in FIG. 1, the appropriate content of charge-generating pigment and trinitro-11H-indeno[1,2-b]quinoxaline-11-one is in the range of 0.1 - 30 wt.% and 1 - 60 wt.%, respectively, and the appropriate thickness of the photosensitive layer is in the range of 5 - 100μ. Further, to the photosensitive layer 2 may be added an appropriate amount of sensitizer as occasion demands.

Figure 1:
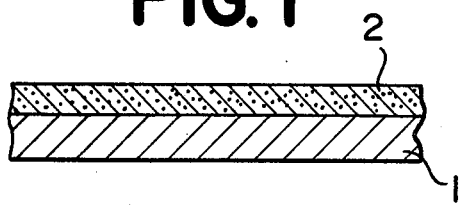
FIG. 1 is an enlarged cross-sectional view of a photoconductive material according to the invention.
Figure 2:
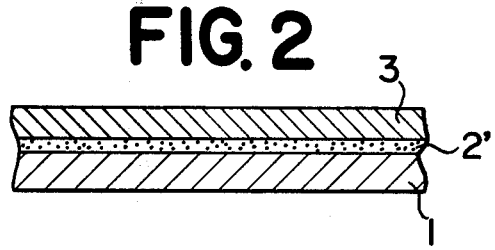
FIG. 2 is an enlarged cross-sectional view of another embodiment of a photoconductive material according to the invention.

On the other hand, the photosensitive material in FIG. 2 is one prepared by forming a thin layer (or photosensitive layer) 2' consisting of charge-generating pigment alone or as mixed with binder resin on a conductive support 1 and further providing thereon a charge-transport layer 3 consisting of trinitro-11H-indeno[1,2-b]quinoxaline-11-one and binder resin. In the case of this photosensitive material, when the photosensitive layer 2' is formed of charge-generating pigment and binder resin, it is desirable to apply the last possible amount of binder resin (to wit, an amount in the range of 40 - 60 wt.% relative to the photosensitive layer). The thickness of the photosensitive layer 2' is in the range of 0.05 - 20μ preferably in the range of 0.1 - 5μ. As for the amount of trinitro-11H-indeno[1,2-b]quinoxaline-11-one to be contained in the charge-transport layer 3, it is desirable to make it as much as possible, but the appropriate amount thereof is in the range of 20 - 60 wt.% when the conditions for preparation of photosensitive material are taken into consideration. And, the applicable grain size of the charge-generating pigment is the same as that in the case of the foregoing photosensitive material (1). The thickness of this charge-transport layer 3 is in the range of 5 - 100μ. Further, like in the case of the two-layer type photosensitive material illustrated in FIG. 1, an appropriate amount of some well-known sensitizer may be added to the three-layer type photosensitive material illustrated in FIG. 2 as well.

Moreover, in both types of photosensitive material according to the present invention, for the purpose of improving the adhesion, electrification characteristic, etc. thereof, a layer of polyamide, vinyl acetate resin, polyurethane and the like or a film of aluminum oxide and the like having a thickness in the range of 0.01 - 1.0μ may be interposed between the support 1 and the photosensitive layer 2 or 2'.

In order to prepare a photosensitive material according to the present invention, in the case of the two-layer type photosensitive material, it will do to follow the procedure comprising dissolving the binder resin in an appropriate solvent, adding the charge-generating pigment together with trinitro-11H-indeno[1,2-b]quinoxaline-11-one to the resulting solution to disperse same thoroughly therein, applying the thus prepared dispersion onto a conductive support and drying thereafter. And, in the case of the three-layer type photosensitive material, it will do to follow the procedure comprising forming a photosensitive layer consisting of the charge-generating pigment alone or a mixture of the charge-generating pigment and the binder resin by depositing through evaporation, coating or a like means on a conductive support and thereafter forming thereon another layer by applying a solution consisting essentially of trinitro-11H-indeno[1,2-b]quinoxaline-11-one and the binder resin by coating or a like means.

A photoconductive sensitive material according to the present invention prepared as above is useful in electrophotography, and it has many advantages such that (a) the sensitivity thereof is so high that it does not give rise to residual potential, (b) it shows little fatigue in repeated use and is stable, and (c) it is easy to manufacture.

DESCRIPTION OF THE PREFERRED EMBODIMENTS

EXAMPLE 1

By crushing Dian Blue [color index (C.I.) 21180] within a ball-mill in the presence of tetrahydrofuran (THF), a dispersion containing 2 wt.% of pigment was prepared. By applying this dispersion by means of a doctor blade onto a polyester film deposited with aluminum through evaporation and subjecting it to natural drying, a 1μ-thick photosensitive layer was formed. Subsequently, by applying a THF solution consisting of 1 part by weight of trinitro-11H-indeno[1,2-b]quinoxaline11-one and 1 part by weight of polycarbonate onto said photosensitive layer by means of a doctor blade and subjecting it to 30 minutes' drying at 100° C. thereby forming a 12μ-thick charge-transport layer, a three-layer type photoconductive sensitive material was prepared.

The thus prepared photosensitive material was next electrified by subjecting it to +6 KV corona discharge for 20 seconds by the use of a commercial electrostatic copying material testing device. After leaving the thus electrified photosensitive material standing in a dark place for 20 seconds, the surface potential Vpo (V) thereat was measured. Subsequently, by exposing it to a tungsten lamp by setting the illumination on the surface of photosensitive material at 20 luxes, recording the decay of the surface potential thereat and the time (seconds) required for said decay by means of a recorder, and seeking the time (seconds) taken in reducing Vpo by half, the amount of exposure E ½ was obtained. That is, E ½ stands for the amount of exposure required for reducing Vpo by half, and denotes the sensitivity. The value of Vpo and E ½ thus obtained was 740 V and 5.1 lux.sec, respectively.

It will be understood from this result of measurement that trinitro-11 H-indeno[1,2-b]quinoxaline-11-one in itself is useful as charge-transport medium.

|  | Vpo (V) | E ½ (lux . sec) |
|---|---|---|
| When charged with positive electricity | 600 | 6 |
| When charged with negative electricity | 570 | 10.0 |

EXAMPLE 2

By depositing selenium on a 300μ-thick aluminum plate to the extent of 1μ in thickness through vacuum evaporation, a photosensitive layer was formed thereon. Subsequently, by applying a THF solution consisting of 1 part by weight of trinitro-11H-indeno[1,2-b]quinoxaline-11-one and 1 part by weight of polyester resin onto said photosensitive layer by means of a doctor blade and subjecting it to natural drying followed by drying under reduced pressure thereby forming a 16μ-thick charge-transport layer, a three-layer type photoconductive sensitive material was prepared.

When the thus prepared photosensitive material was evaluated with respect to Vpo and E ½ in the same way as in Example 1, in the case where it was charged with positive electricity, the value of Vpo was 960 V and the value of E ½ was 6.3 lux.sec.

EXAMPLE 3

After crushing 1 part by weight of B type copper phthalocyanine within a ball-mill in the presence of THF, by adding thereto 12 parts by weight of trinitro-11H-indeno[1,2-b]-quinoxaline-11-one and 18 parts by weight of polyester resin, a dispersion was prepared. Subsequently, by applying this dispersion by means of a doctor blade onto a polyester film deposited with aluminum through evaporation and subjecting it to 30 minutes' drying at 100°C., a two-layer type photoconductive sensitive material having a 22μ-thick photosensitive layer was prepared.

When the thus prepared photosensitive mateial was evaluated with respect to Vpo and E ½ in the same way as in Example 1, the value of Vpo was 940 V and the value of E ½ was 8.7 lux.sec.

What is claimed is:

1. An electrophotographic plate comprising an electrically conductive support coated with a photoconductive layer having a thickness of from 5 to 100 microns, said photoconductive layer consisting essentially of a mixture of from 0.1 to 30 percent by weight of charge-generating pigment having a particle size of less than 5 microns and selected from the group consisting of azo dye, xanthene dye, violanthrone dye, phthalocyanine dye, indigoid dye, perylene dye, indanthrone dye, Se, SeTe, CdS and CdSe, from 1 to 60 percent by weight of trinitro-11H-indeno[1,2-b]quinoxaline-11-one and the balance is essentially a binder resin selected from the group consisting of polyester resin, polycarbonate resin, acrylic resin, silicone resin, novolac resin and ketone resin.

2. An electrophotographic plate comprising an electrically conductive support and a photoconductive layer coated on said support, said photoconductive layer consisting essentially of a mixture of charge-generating pigment, trinitro-11H-indeno[1,2-b]quinoxaline-11-one and binder resin which does not form a charge-transport complex with said trinitro-11H-indeno-[1,2-b]-quinoxaline-11-one.

3. An electrophotographic plate according to claim 2, wherein said charge-generating pigment is selected from the group consisting of azo dye, xanthene dye, violanthrone dye, phthalocyanine dye, indigoid dye, perylene dye, indanthrone dye, Se, SeTe, CdS and CdSe.

4. An electrophotographic plate according to claim 2, wherein said binder resin is selected from the group consisting of polyester resin, polycarbonate resin, acrylic resin, silicone resin, novolac resin and ketone resin.

5. An electrophotographic plate according to claim 2, wherein the grain size of said charge-generating pigment is less than 5μ.

6. An electrophotographic plate according to claim 2, wherein the amounts of said charge-generating pigment and trinitro-11H-indeno[1,2-b]quinoxaline-11-one are in the range of 0.1 – 30% and 1 – 60%, respectively, based on the total weight of the photoconductive layer.

7. An electrophotographic plate according to claim 2, wherein the thickness of said photoconductive layer is in the range of 5 – 100μ.

8. An electrophotographic plate according to claim 2, wherein an additional film formed of a member selected from the group consisting of polyamide, vinyl acetate resin, polyurethane and aluminum oxide is interposed between the support and the photoconductive layer.

9. An electrophotographic plate according to claim 8, wherein the thickness of said additional film is in the range of 0.01 – 1.0μ.

10. An electrophotographic plate comprising an electrically conductive support, a photoconductive layer coated on said support and a charge-transport layer coated on said photoconductive layer, said photoconductive layer having a thickness of from 0.05 to 20 microns and consisting essentially of charge-generating pigment or a mixture of charge-generating pigment and from 40 to 60 percent by weight of binder resin, wherein said charge-generating pigment has a particle size of less than 5 microns and is selected from the group consisting of azo dye, xanthene dye, violanthrone dye, phthalocyanine dye, indigoid dye, perylene dye, indanthrone dye, Se, SeTe, CdS and CdSe and wherein said binder resin is selected from the group consisting of polyester resin, polycarbonate resin, acrylic resin, silicone resin, novolac resin and ketone resin, said charge-transport layer having a thickness of from 5 to 100 microns and consisting essentially of a mixture of from 20 to 60 percent by weight of trinitro-11H-indeno[1,2-b]quinoxaline-11-one and the balance is essentially said binder resin.

11. An electrophotographic plate comprising an electrically conductive support, a photosensitive layer coated on said support and a charge-transport layer coated on said photosensitive layer, said photosensitive layer consisting essentially of chargegenerating pigment or a mixture of charge-generating pigment and binder resin, said charge-transport layer consisting essentially of a mixture of trinitro-11H-indeno[1,2-b]quinoxaline-11-one and binder resin which does not form a charge-transport complex with said trinitro-11H-indeno[1,2-b]quinoxaline-11-one.

12. An electrophotographic plate according to claim 11, wherein said charge-generating pigment is selected from the group consisting of azo dye, xanthene dye, violanthrone dye, phthalocyanine dye, indigold dye, perylene dye, indanthrone dye, Se, SeTe, CdS and CdSe.

13. An electrophotographic plate according to claim 11, wherein said binder resin is selected from the group consisting of polyester resin, polycarbonate resin, acrylic resin, silicone resin, novolac resin and ketone resin.

14. An electrophotographic plate according to claim 11, wherein the grain size of said charge-generating pigment is less than 5µ.

15. An electrophotographic plate according to claim 11, wherein the amount of said trinitro-11H-indeno[1,2-b]quinoxaline-11-one is in the range of 20 - 60% based on the total weight of the charge-transport layer..

16. An electrophotographic plate according to claim 11, wherein the thickness of said photoconductive layer is in the range of 0.05 - 20µ.

17. An electrophotographic plate according to claim 11, wherein the thickness of said charge-transport layer is in the range of 5 - 100µ.

18. An electrophotographic plate according to claim 11, wherein said photoconductive layer contains binder resin.

19. An electrophotographic plate according to claim 18, wherein said binder resin is selected from the group consisting of polyester resin, polycarbonate resin, acrylic resin, silicone resin, novolac resin and ketone resin.

20. An electrophotographic plate according to claim 18, wherein the amount of said binder resin contained in said photoconductive layer is in the range of 40 - 60% based on the total weight of the photoconductive layer.

21. An electrophotographic plate according to claim 11, wherein an additional film formed of a member selected from the group consisting of polyamide, vinyl acetate resin, polyurethane and aluminum oxide is interposed between the support an the photoconductive layer.

22. An electrophotographic plate according to claim 21, wherein the thickness of said additional film is in the range of 0.01 - 1.0µ.

* * * * *

UNITED STATES PATENT AND TRADEMARK OFFICE
CERTIFICATE OF CORRECTION

PATENT NO.   :   4 148 638
DATED        :   April 10, 1979
INVENTOR(S)  :   Masafumi Ohta et al It is certified that error appears in the above-identified patent and that said Letters Patent are hereby corrected as shown below:

Column 7, line  5;  change "chargegenerating" to ---charge-generating---.
Column 7, line 16;  change "indigold" to ---indigoid---.
Column 8, line 25;  change "an" to ---and---.
Column 8, line  4;  change "photoconductive" to ---photosensitive---.
Column 8, line 10;  change "photoconductive" to ---photosensitive---.
Column 8, line 19;  change "photoconductive" to ---photosensitive---.
Column 8, line 20;  change "photoconductive" to ---photosensitive---.
Column 8, line 25;  change "photoconductive" to ---photosensitive---.

Signed and Sealed this

Seventeenth Day of July 1979

[SEAL]

Attest:

LUTRELLE F. PARKER
*Attesting Officer*   *Acting Commissioner of Patents and Trademarks*